(12) United States Patent
Sela et al.

(10) Patent No.: US 11,426,365 B2
(45) Date of Patent: Aug. 30, 2022

(54) COMPOSITIONS COMPRISING THYMOQUINONE AND OMEGA-3 FATTY ACIDS

(71) Applicant: TRINUTRA LTD., Nes Ziona (IL)

(72) Inventors: Yoram Sela, Ra'anana (IL); Mor Zeilkha, Ramat Gan (IL); Itschak Lamensdorf, Modi'in (IL)

(73) Assignee: Trinutra Ltd., Nes Ziona (IL)

( * ) Notice: Subject to any disclaimer, the term of this patent is extended or adjusted under 35 U.S.C. 154(b) by 0 days.

(21) Appl. No.: 16/631,037

(22) PCT Filed: Jul. 15, 2018

(86) PCT No.: PCT/IL2018/050775
§ 371 (c)(1),
(2) Date: Jan. 14, 2020

(87) PCT Pub. No.: WO2019/016794
PCT Pub. Date: Jan. 24, 2019

(65) Prior Publication Data
US 2020/0138743 A1    May 7, 2020

Related U.S. Application Data

(60) Provisional application No. 62/533,024, filed on Jul. 15, 2017.

(51) Int. Cl.
| | | |
|---|---|---|
| *A61K 36/00* | (2006.01) | |
| *A61K 31/122* | (2006.01) | |
| *A61P 29/00* | (2006.01) | |
| *A61K 31/202* | (2006.01) | |
| *A61K 31/404* | (2006.01) | |
| *A61K 36/53* | (2006.01) | |
| *A61K 36/71* | (2006.01) | |

(52) U.S. Cl.
CPC .......... *A61K 31/122* (2013.01); *A61K 31/202* (2013.01); *A61K 31/404* (2013.01); *A61K 36/53* (2013.01); *A61K 36/71* (2013.01); *A61P 29/00* (2018.01)

(58) Field of Classification Search
CPC ................. A61P 29/00; A61K 36/71
See application file for complete search history.

(56) References Cited

U.S. PATENT DOCUMENTS

2006/0264497 A1 * 11/2006 Zeligs .................... A61Q 11/00
                                                       514/414
2014/0213558 A1 *  7/2014 Crede .................... A61K 31/59
                                                       514/164

FOREIGN PATENT DOCUMENTS

| EP | 2 285 242 | 5/2013 | |
|---|---|---|---|
| KR | 10-2014-0006376 | 1/2014 | |
| WO | 2013/030669 | 3/2013 | |
| WO | WO-2013030669 A2 * | 3/2013 | ........... A61K 31/355 |

OTHER PUBLICATIONS

Breyer et al., "Effects of thymoquinone—Fatty acid conjugates on cancer cells", ChemMedChem, vol. 4, No. 5, May 11, 2009, pp. 761-768.
Fayez et al., "Beneficial effects of thymoquinone and omega-3 on intestinal ischemia/reperfusion-induced renal dysfunction in rats", Bulletin of Faculty of Pharmacy, vol. 52, No. 2, 2014, pp. 171-177.
Nauroth et al., "Docosahexaenoic Acid (DHA) and Docosapentaenoic Acid (DPAn-6) Algal Oils Reduce Inflammatory Mediators in Human Peripheral Mononuclear Cells In Vitro and Paw Edema In Vivo", Lipids, vol. 45, No. 5, Apr. 30, 2010, pp. 375-384.
Rahmani et al., "Nigella sativa and its active constituents thymoquinone shows pivotal role in the diseases prevention and treatment", Asian Journal of Pharmaceutical and Clinical Research, vol. 8, No. 1, 2015, pp. 48-53.
Abstract of KR 2014-0006376, Database WPI, Week 201409, Thomson Scientific, XP002785307, Jan. 16, 2014.
International Search Report for PCT/IL2018/050775, dated Oct. 19, 2018, 4 pages.
Written Opinion of the ISA for PCTIL2018/050775, dated Oct. 19, 2018, 6 pages.

* cited by examiner

*Primary Examiner* — Qiuwen Mi
(74) *Attorney, Agent, or Firm* — Nixon & Vanderhye P.C.

(57) ABSTRACT

The present invention provides a composition comprising a synergistic combination of thymoquinone and one or more omega-3 fatty acids, wherein the molar ratio between said thymoquinone and said one or more omega-3 fatty acids is at least 1:7. The present invention also provides a method of using said composition to treat or prevent inflammatory conditions.

14 Claims, 4 Drawing Sheets

COMPOSITIONS COMPRISING THYMOQUINONE AND OMEGA-3 FATTY ACIDS

This application is the U.S. national phase of International Application No. PCT/IL2018/050775 filed 15 Jul. 2018, which designated the U.S. and claims the benefit of U.S. Patent Application No. 62/533,024 filed 15 Jul. 2017, the entire contents of each of which are hereby incorporated by reference.

BACKGROUND OF THE INVENTION

Black Cumin (BC) and Thymoquinone (TQ)

*Nigella sativa*, commonly known as black cumin (BC), is an annual flowering plant native to Mediterranean countries. Its seed oil had been used in traditional herbal medicine for the treatment of arthritis, lung diseases and hypercholesterolemia immune, inflammation and skin disease. The BC products have been used orally and topically, and clinical studies have shown that the biological activity of *Nigella sativa* seeds is mainly attributed to its main essential oil component, thymoquinone (TQ):

TQ has been investigated for its antioxidant, anti-inflammatory and anticancer activities in both in vitro and in vivo models. Its anti-oxidant/anti-inflammatory effect has been reported in various disease models, including encephalomyelitis, diabetes, asthma and carcinogenesis. The anticancer effect(s) of TQ are mediated through different modes of action, including antiproliferation, apoptosis induction and other modes of action.

Omega 3

The essential polyunsaturated fatty acids (PUFAs) comprise 2 main classes: n-6 and n-3 fatty acids. The most common source of n-6 fatty acids is linoleic acid (LA), which is found in high concentrations in various vegetable oils. Arachidonic acid (AA), the 20-carbon n-6 fatty acid, is obtained largely by synthesis from LA in the body.

Omega-3 fatty acids are considered essential fatty acids. They are essential to human health but cannot be manufactured by the body. For this reason, omega-3 fatty acids must be obtained from food. Omega-3 fatty acids can be found in fish, such as salmon, tuna, and halibut, other marine life such as algae and krill, certain plants (including purslane), and nut oils. Omega-3 fatty acids play a crucial role in brain function as well as normal growth and development. There are three major types of omega 3 fatty acids that are ingested in foods and used by the body: alpha-linolenic acid (ALA), eicosapentaenoic acid (EPA), and docosahexaenoic acid (DHA). Once ingested, the body converts ALA to EPA and DHA, the two types of omega-3 fatty acids more readily used by the body.

Both n-3 and n-6 fatty acids are incorporated into cellular phospholipid membranes, where they serve as precursors to the production of eicosanoids, such as prostaglandins, leukotrienes, and thromboxanes. Eicosanoid metabolites of n-3 fatty acids are less atherogenic, proinflammatory, and vasoconstrictive than are the eicosanoids from n-6 fatty acids. For example, prostaglandin $E_2$, thromboxane $A_2$, and leukotriene $B_4$ are derived from AA by cyclooxygenase and lipoxygenase enzymes and are well-described mediators of platelet aggregation, immune response, and vasoreactivity. Conversely, EPA is metabolized by cyclooxygenase and lipoxygenase to prostaglandin $E_3$ and leukotriene $B_5$, which are lesser promoters of platelet aggregation and immune reactivity. Omega 3 fatty acids in dietary fish oil are reported to have anti-inflammatory and anti-thrombogenic and anti-arrhythmic effects in humans. Fish oil significantly diminishes the production and effectiveness of various prostaglandins, naturally occurring hormone-like substances that can accentuate inflammation and thrombosis.

Dietary fish oil causes its prostaglandin-lowering effects through three different mechanisms: firstly, much fewer prostaglandins are made in the body from omega 3 fatty acids as compared to the other class of fatty acids, the omega 6 family of fatty acids that originate in the diet from leafy vegetables and other plant sources. Secondly, the omega 3 fatty acids compete with omega 6 fatty acids for the same binding site on the COX 1 enzyme that converts the omega 6 fatty acids to prostaglandin (which is why the COX 1 enzyme and its COX 2 cousin are the targets of anti-inflammatory drugs like ibuprofen). The more omega 3 fatty acids present to block the binding sites, the fewer omega 6 fatty acids are able to be converted to prostaglandin. Thirdly, although omega 3 fatty acids are also converted to prostaglandins, the prostaglandins formed from omega 3 are generally 2 to 50 times less active than those formed from the omega 6 fatty acids from dietary plants. Omega-3 fatty acids are commercially available as prescription drugs in the US under the trademark Lovaza and in Europe and elsewhere as Omacor. Lovaza is predominantly a mixture of ethyl esters of eicosapentaenoic acid (EPA—approximately 465 mg) and docosahexaenoic acid (DHA—approximately 375 mg), each capsule containing at least 900 mg of omega-3 fatty acids.

3,3'-Diindolylmethane (DIM)

DIM is a naturally occurring compound found in cruciferous vegetables (Brassicaceae) like broccoli, cauliflower, cabbage, Brussels sprouts and kale. It has a molecular weight of 246 and is pale yellow in crystalline form. The purified compound does not have any taste.

Figure 1:
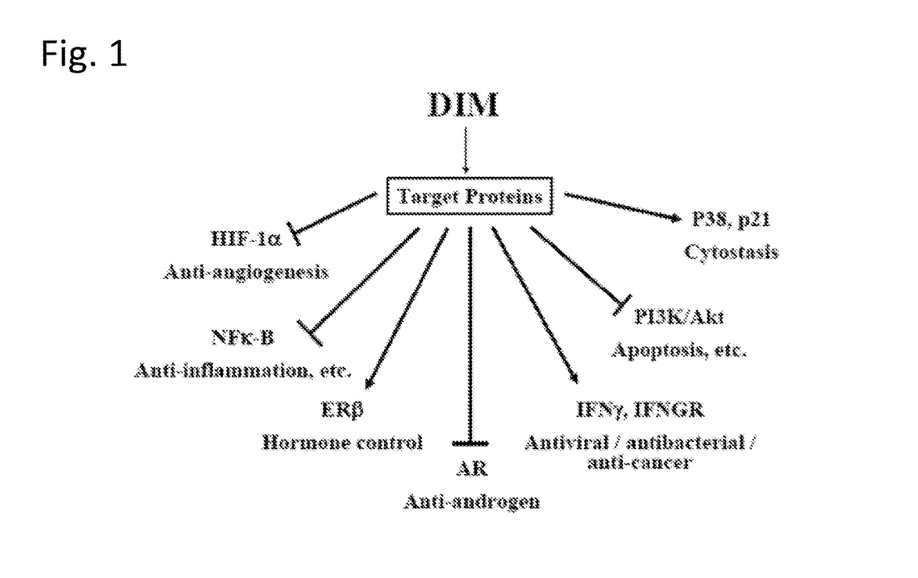
FIG. 1 is a chart depicting some of the known biological effects of DIM.

DIM is a compound derived from the digestion of indole-3-carbinol, found primarily in the above-mentioned vegetables. The biological effects of DIM are depicted in the chart presented in FIG. 1.

Due to its various potent anti-cancer properties, the US National Cancer Institute has begun clinical trials of DIM as a therapeutic agent for numerous forms of cancer.

Furthermore, due to its innate immune modulating properties (potentiation of interferon-gamma receptors and production), DIM is also being investigated as a possible treatment for a variety of viral infections and antibiotic resistant bacteria.

Indole-3-carbinol (I3C) is an autolysis product of glucosinolate present in *Brassica* plants such as turnips, kale, broccoli, cabbage. Brussels sprouts, and cauliflower. It has been shown to be protective against several cancers. When I3C is exposed to gastric acid, it is converted to many self-condensation products, among which 3,3'-diindolylmethane (DIM) is the major product. DIM was readily detected in the liver and feces of rodents fed I3C, whereas the original I3C was not detected in these animals. In addition, DIM is gradually formed from I3C in cell culture at a neutral pH over extended incubation periods. Furthermore, it has been reported that in women who underwent a phase I trial, I3C itself was not detectable in plasma after I3C administration and that the only detectable I3C-derived product was DIM. These results suggest that DIM, not I3C, may mediate the observed physiological effects of dietary I3C.

Although many substances—both manufactured pharmaceuticals and products of nature—have been found to possess anti-inflammatory properties, a need still exists for therapeutic compositions having higher efficacy and potency and lower adverse effects than existing treatment regimes. The present invention meets this need.

SUMMARY OF THE INVENTION

The present invention is primarily directed to a composition comprising a combination of TQ and one or more omega-3 fatty acids, wherein the molar ratio between said TQ and said one or more omega-3 fatty acids is at least 1:7.

It is to be noted that the term 'composition' as used herein refers to any physical form that may be administered to human and non-human species, including (but not limited to) pharmaceutical dosage forms, foodstuffs and beverages, additives and supplements for foodstuffs and beverages, and nutraceuticals.

For the purposes of the composition of the present invention, the omega-3 fatty acids are generally present in the form of free fatty acids, ethyl esters, or combinations thereof. In certain embodiments, however, the omega-3 fatty acids may be present in the forms of triglycerides and/or phospholipids.

Preferably, the molar ratio between TQ and the omega-3 fatty acids in the presently-disclosed composition is in the range of 1:7-1:200.

In some cases, the molar ratio between TQ and the omega-3 fatty acids is in the range of 1:7-1:150.

In other embodiments, the molar ratio between TQ and the omega-3 fatty acids is in the range of 1:7-1:140.

In still further embodiments, the molar ratio between TQ and the omega-3 fatty acids is in the range of 1:7-1:70

In other embodiments, the molar ratio between TQ and the omega-3 fatty acids is in the range of 1:7-1:40.

In yet further embodiment, the molar ratio between TQ and the omega-3 fatty acids is in the range of 1:30-1:150.

The molar ratios disclosed hereinabove and demonstrated in the working examples provided hereinbelow, are generally those that result in a synergistic interaction between TQ and omega-3 fatty acids, with respect to the anti-inflammatory effects of the composition of the present invention.

In some cases, the composition of the invention disclosed herein may further comprise DIM, and/or its precursor indole-3-carbinol (I3C).

In one highly-preferred embodiment of the present invention, BC is the main or sole source of TQ. In such cases, TQ may be present in a form selected from the group consisting of intact BC seeds, ground BC seeds. BC seed oil, solvent extracts of BC seeds, supercritical $CO_2$ extracts of BC oils, and/or partially purified extracts, purified extracts and/or fractions thereof. However, other forms of BC (such as extracts of various portions of the BC plant) may also be used to provide the TQ for the present composition.

Alternatively, the source of TQ in the presently-disclosed composition may be the oregano plant, specifically plants of the *Origanum* genus, more preferably species such as *O. vulgare* and *O. syriacum*, but also including other known species, subspecies and variants of oregano. In this embodiment. TQ may be present in the composition in a form selected from the group consisting of intact oregano seeds, ground oregano seeds, oregano seed oil, solvent extracts of oregano seeds, supercritical $CO_2$ extracts of oregano oils, oregano plant extracts and/or partially purified extracts, purified extracts and/or fractions thereof.

In addition, the TQ used in the composition of the present invention may be obtained from a variety of other plant sources, including various plant species of Asteraceae, Cupressaceae, Lamiaceae, and Ranunculaceae families In another embodiment, the TQ in the composition is synthetic TQ.

In a highly-preferred embodiment of the composition of the present invention, TQ is present in the form of cold-pressed BC seed oil.

Various different omega-3 fatty acids (either separately or in combination) may be used in the compositions of the present invention, including the following compounds:

Hexadecatrienoic acid (HTA), α-Linolenic acid (ALA), Stearidonic acid (SDA), Eicosatrienoic acid (ETE), Eicosatetraenoic acid (ETA), Eicosapentaenoic acid (EPA), Heneicosapentaenoic acid (HPA), Docosapentaenoic acid (DPA), Clupanodonic acid, Docosahexaenoic acid (DHA), Tetracosapentaenoic acid, and Tetracosahexaenoic acid (Nisinic acid)

More preferably, the one or more omega-3 fatty acids are selected from the group consisting of eicosapentaenoic acid (EPA), docosahexanoic (DHA) and alpha-linolenic acid (ALA).

In some cases, the omega-3 fatty acids are present in the composition in the form of highly concentrated oils containing a minimum of 50% w/w DHA & EPA in their free fatty acid or ethyl ester forms, and wherein the molar ratio between DHA and EPA is in the range of 1:1000 to 1000:1.

In another aspect, the present invention is directed to a dosage form comprising the composition according to claim 1, wherein said dosage form is selected from the group consisting of a soft gelatin capsule, a sprinkle capsule, a sachet, a tablet, a syrup or other pharmaceutically acceptable oral dosage form.

In a preferred embodiment of the above-mentioned dosage forms, the amount of TQ present is in the range of 1-15% (w/w) of the amount of omega-3 fatty acid(s). Generally, the amount of TQ in each dosage form is in the range of 0.1-5,000 mg. The amount of omega-3 fatty acid in each dosage form is generally in the range of 0.5-10,000 mg.

In a further aspect, the present invention is directed to a method for the treatment, prevention, attenuation or inhibition of the progression of an inflammatory disease or a disease having an inflammatory component in a mammalian subject, comprising the administration of a composition of the present invention, as disclosed hereinabove and described in more detail hereinbelow. In a preferred embodiment, the mammalian subject is a human subject.

The term 'a disease having an inflammatory component' should be understood as referring to any disease or health disorder, in which inflammatory processes may form part of the pathogenic process. These may include conditions which are not primarily considered to be inflammatory diseases, such as various types of neoplastic conditions and certain metabolic disorders, cardiac disease, and so on.

In the method of the present invention, the daily dosage of TQ administered to the subject generally constitutes approximately 1-15% (w/w) of the amount of administered omega-3 fatty acid(s). The total daily amount of TQ administered to the subject may be in the range of 0.1-5,000 mg, while the total daily amount of omega-3 fatty acid is generally in the range of 0.5-10,000 mg.

In some embodiments of the presently-disclosed method, the inflammatory disease may be selected from the group consisting of rheumatoid arthritis, pelvic inflammatory disease, atherosclerosis, periodontitis, ulcerative colitis, Crohn's disease, psoriasis, multiple sclerosis, AMD, other possible eye inflammatory related diseases, inflammatory bowel disease and asthma.

The present invention also encompasses a composition as defined herein for use as a medicament.

The present invention is also directed to a composition as defined hereinabove and described hereinbelow for use in the treatment, prevention, attenuation or inhibition of the progression of an inflammatory disease or a disease having an inflammatory component.

In another aspect, the present invention is directed to the use of a composition as described and defined herein in the preparation of a medicament for the treatment, prevention, attenuation or inhibition of the progression of an inflammatory disease or a disease having an inflammatory component.

Furthermore, in certain preferred embodiments, the composition additionally comprises diindolylmethane (DIM), and/or its precursor indole-3-carbinol (I3C) These and other aspects of the invention will become apparent from the description of the invention which follows below.

DETAILED DESCRIPTION OF THE INVENTION

The present invention provides a novel combination composition, comprising two actives: TQ and omega-3 fatty acids or esters. In one embodiment, said composition further comprises DIM. This composition is active as an immune modulating and anti-inflammatory agent. Preferably, the molar ratios between the TQ and the omega-3 fatty acids are chosen such that there is a measurable synergistic interaction between those two components, with respect to the anti-inflammatory activities of the composition.

The compositions of the present invention may be used to treat or prevent many different inflammatory conditions and diseases, including, but not limited to rheumatoid arthritis (RA), inflammatory bowel disease (IBD), asthma, pelvic inflammatory disease, atherosclerosis, periodontitis, ulcerative colitis. Crohn's disease, psoriasis and multiple sclerosis.

In one embodiment, there are provided fixed dose compositions for the systemic treatment or prevention of inflammatory diseases, comprising TQ and omega-3 fatty acids or their esters, preferably ethyl esters. In another embodiment, the fixed dose composition comprises BC-concentrated TQ, 3,3-diindolylmethane (DIM) and omega-3 fatty acids or their esters, preferably ethyl esters. These compositions may further comprise other nutritionally or pharmaceutically acceptable ingredients, including, but not limited to antioxidants, preferably oil-soluble antioxidants, selected from ascorbic acid, vitamin E, tocopherol, BHA, BHT, vitamin E TPGS, surface active materials selected from the group comprising Span, lecithin, Brij, sucrose esters (preferably those with low HLB values) and mixtures thereof.

The amount of TQ in unit-dosage forms of the composition of the present invention may vary from 0.1-5,000 mg, preferably from 20 mg to 350 mg, more preferably 50-110 mg. When present, the DIM dosage in the unit-dosage forms may vary from 10 mg to 200 mg, preferably between 30 mg and 200 mg and most preferably between 30 mg and 100 mg of DIM per dose unit. The DIM used in the compositions is preferably of the purified pharmaceutically acceptable quality, having an assay in excess of 99.0%, preferably more than 99.5% and most preferably in excess of 99.7%. DIM used for the manufacture of the instant compositions will be optionally micronized or preferably nanosized. In some embodiments, the amount of DIM in the dosage forms and/or compositions of the present invention is 1-15% of the amount of omega-3 fatty acid.

The omega-3 fatty acids—either in their free fatty acid form or as esters (preferably ethyl esters)—are present in the unit-dosage forms in an amount in the range of 0.5-10,000 mg, preferably from 200 mg to 2000 mg, more preferably between 500 mg and 900 mg and most preferably between 600 mg and 850 mg.

The omega-3 fatty acids or esters in the compositions of this invention contain predominantly EPA and DHA, in ratios that may vary between 1:1000 and 1000:1. The esters may be triglycerides or lower alkyl esters, preferably ethyl esters of the omega-3 fatty acids. In some cases, the ratio between EPA and DHA will be in the range between 1:2 and 2:1, between 2:1 and 1:1, between 1.5:1 and 1:1 or 1.25:1. In other cases, pure or almost pure EPA or DHA in their different forms may be used. In addition, other omega-3 fatty acids (included those listed hereinabove) may be used to prepare the compositions of the present invention.

The mixtures of the EPA/DHA ethyl esters are oils, preferably highly concentrated oils, containing at least 50% DHA & EPA ethyl esters, preferably 85% or more of DHA & EPA ethyl esters. The compositions of this invention, comprising DIM, omega-3 fatty acid esters and optionally other naturally origin entities synergistically act entities, will be administered in effective doses, in the form of defined pharmaceutical dosage forms, or in other forms suitable for use as nutraceuticals, food and beverages, additives for food and beverages, and so on. The composition may be administered or consumed either once daily, or several times each day.

In one embodiment, the compositions may be administered in the form of soft gelatin capsules (SGC), sprinkle capsules, sachets, tablets or syrup or any other commonly used and pharmaceutically acceptable oral dosage forms.

The soft gelatin capsules (SGC) may, in one embodiment, comprise about 10-200 mg of the TQ/fatty acid esters combination. One example of SGC composition is as follows:
 a. 10-200 mg TQ in each SGC.
 b. 300-900 mg of highly concentrated EPA & DHA triglycerides or preferably their EE (ethyl esters; minimum 50% w/w), with EPA/DHA ratios from 1:2-2:1
 c. Optionally 1-20 mg of lycopene/lutein or combination of lutein and other naturally origin entity.
 d. Optionally 4-8 mg Vitamin E (or an alternative antioxidant)
 e. Optionally surface active materials like Span, vitamin E TPGS, lecithin or similar In another embodiment, the SGC formulation may comprise about 0.1-2 grams of the TQ/DIM/fatty acid ester combination. An exemplary composition is detailed in the following:
 a. 10-200 mg TQ in each SGC.
 b. 10-200 mg DIM (preferably micronized or nanosized) in each SGC.
 c. 300-900 mg of highly concentrated EPA & DHA triglycerides or preferably their EE (minimum 50% w/w), with EPA/DHA ratios from 1:2-2:1
 d. Optionally 1-20 mg of lycopene/lutein or combination of lutein and other naturally origin entity.
 e. Optionally 4-8 mg Vitamin E (or an alternative antioxidant)
 f. Optionally surface active materials like Span, vitamin E TPGS, lecithin or similar The compositions of this invention may be manufactured by a process comprising
 a. Weighing omega-3 oil.
 b. Adding the TQ.
 c. Adding the inactive ingredients selected from antioxidants and surface active materials.
 d. Mixing until all components dissolve in the oil.
 e. Optionally adding micronized or nanosized DIM in oil mixture (such as MCT oil and TPGS) to the oily mixture.
 f. Mixing until fully dissolved or suspended;
 g. Optionally heating up to 50 deg C., for less than two hrs. under nitrogen blanketing.
 h. Filling in soft gelatin capsules.

All of the above stages are optionally carried out under nitrogen blanketing.

Various alternative methods for preparing the composition of the present invention may also be used.

In another embodiment, there is provided a method of treatment of a patient in need thereof for the treatment, prevention, attenuation or inhibition of the progression of an inflammatory disease by administration of a synergistic fixed dose combination of TQ and an omega-3 fatty acid or its ethyl ester.

In a further embodiment of the above-disclosed method, the synergistic fixed dose combination further comprises 3,3-diindolylmethane (DIM).

When present in the fixed dose compositions, the DIM is preferably in a micronized or nanosized form.

The fixed dose compositions of the instant invention are administered in the form of a soft gelatin capsule, a sprinkle capsule, a sachet, a tablet, bulk powder, solution or a syrup or other pharmaceutically acceptable oral dosage form.

The other nutritionally and pharmaceutically acceptable ingredients present in the compositions may include antioxidants (preferably oil-soluble antioxidants) selected from the group comprising ascorbic acid, vitamin E, tocopherol, BHA, BHT, vitamin E TPGS and mixtures thereof and surface active materials selected from the group comprising Span, lecithin, Brij, sucrose esters (preferably those with low HLB values) and mixtures thereof. Carotenoids including (but not limited to) lutein and lycopene can be added as well, for their additional health benefits.

The methods claimed in this invention are intended for use in the treatment and/or prevention of inflammatory diseases, including (but not limited to) those belonging to the group comprising rheumatoid arthritis, pelvic inflammatory disease, atherosclerosis, periodontitis, ulcerative colitis, Crohn's disease, psoriasis, multiple sclerosis, inflammatory bowel disease and asthma.

It is appreciated that certain features of the invention which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specific examples of the present invention will now be described in the following working examples. While these examples illustrate and exemplify some of the key features of the present invention, they do not limit its scope in any way.

EXAMPLES

Example 1

Formulation Containing Omega-3 Oil, BC Oil and DIM

Weigh 500 gr of highly concentrated omega-3 oil containing 50% w/w EPA&DHA EE in a ratio of approximately 1:1.

Add 50 gr of micronized DIM. 50 gr standardized BC oil and 10 gr of vitamin E TPGS Mix under nitrogen for one hour and fill into soft gelatin capsules (SGC), 50 mg DIM, 45 mg BC and 450 mg omega 3 EE's mixture per capsule.

EPA&DHA EE

This product was supplied as ROPUFA®'75' n-3 EE Oil
ROPUFA® '75' n-3 EE Oil is an oily liquid with a very faint, fish like odor.

It contains at least 75% n-3 polyunsaturated fatty acids (PUFAs) in the form of ethyl esters, predominantly as eicosapentaenoic acid (EPA) and docosahexaenoic acid (DHA).

It is stabilized with Mixed Tocopherols and Ascorbyl palmitate. Rosemaiy extract is used as a processing aid.

Specification
 Appearance: oily liquid
 Color: yellowish
 Acid value: max. 3.0 mg KOH/g
 Peroxide value: max. 5.0 mEq/kg
 p-Anisidine value: max. 10
 Totox number: max. 20.0

Absorbance (at 233 nm): max. 0.60
Water: 1.0%
EPA content (area percent): min. 42%
DHA content (area percent) min 22%

Example 2

A Formulation Containing Omega-3 Oil, BC Oil and DIM

Weigh 1000 gr of highly concentrated omega 3 oil containing 75% w/w EPA&DHA EE's in a ratio of 1.2:1.

Add 150 gr micronized DIM. 30 g lecithin, 50 gr standardized BC oil and 20 gr vitamin E TPGS Mix under nitrogen for one hour and fill into soft gelatin capsules (SGC), filling 1000 mg of the above mixture in each capsule Prepare the SGC of Examples 1-2 According to the Following Process:

Add lutein, antioxidants like vitamin E, C, or similar, surface active materials like lecithin to the omega 3 oil.

Mix until all components dissolve in the oil.

Add the micronized/nanosized DIM to the oily mixture.

Mix until fully dissolved or suspended; if required heat up to 50 deg C., for no longer than two hours.

Fill in soft gelatin capsules.

Perform the above mentioned process under nitrogen blanket.

Example 3

Dose-Dependent Inhibition of Nitric Oxide (NO) Production by BC Oil Containing Different Concentrations of TO As mentioned hereinabove, the present inventors have now found that BC preparations containing greater than about 0.6% TQ are significantly more active as anti-inflammatory agents than BC containing concentrations of TQ lower than this level.

The following study was conducted using (i) a fresh cold press extract of BC containing 1.1% TQ from Ness Oil, Israel, and (ii) a second extract sourced from Ness oil containing 0.3% TQ.

The fatty acid content of both preparations was measured, and both products were found to have the same fatty acid profile:

Fatty Acid Profile:
 Myristic Acid: 2.4%
 Palmitic Acid: 13.0%
 Stearic Acid: 2.3%
 Oleic Acid: 23.1%
 Linolic Acid: 53.2%
 Linolenic Acid: 1.0%
 Others: 4.2%
 Total PUFA: 54.2%.

These two different BC preparations were then tested for their ability to inhibit NO production, in accordance with the method described hereinbelow in Example 4.

Figure 2:
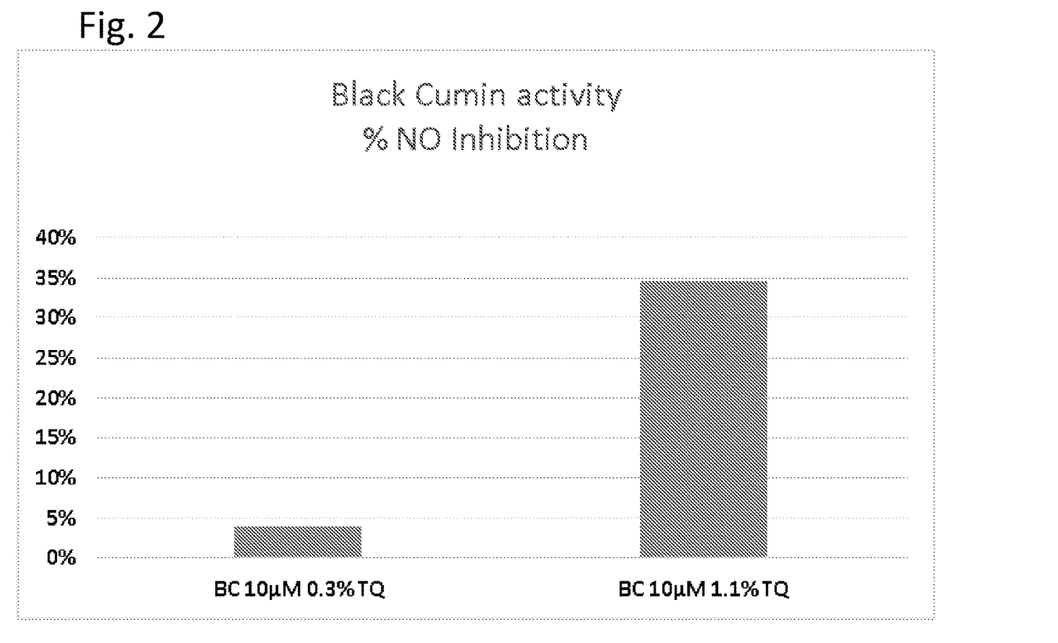
FIG. 2 graphically depicts the result of a comparative study in which a significantly greater anti-inflammatory effect is seen when the composition of the invention is prepared using a BC oil containing a high concentration of TQ.

The results of this comparative study are shown in FIG. 2. It may be seen from this figure that the BC preparation containing 1.1% TQ caused an inhibition of NO production that was approximately 7-fold greater than that caused by the more commonly used BC preparation containing 0.3% TQ. In view of this significant difference between the two preparations, for the purpose of the present invention, only BC preparations having greater than 0.6%, and more preferably greater than 1% concentrations of TQ were used.

Example 4

Cytokine Release Study

BC-concentrated TQ (obtained from TriNutra. Ness Ziona, Israel), Omega-3 oil (fish oil—FO) and Diindolylmethane (DIM) were tested on a macrophage murine cellular system (RAW 264.7) before stimulation with Lipopolysaccharide (LPS), an endotoxin which induces a strong response from normal animal immune systems. The inflammatory effect was demonstrated by the production of Nitric Oxide (NO), which was measured by Griess reagent which detects nitrite (NO2) production.

Test Procedures

Cell Culturing

Cells were thawed, grown and managed according to standard protocols.

On Day 0, cells were seeded in 6-well plates at concentrations of $6 \times 10^5$. Volume of medium per well was 2 ml. Cells were seeded in triplicates for each treatment and for each control.

Formulations

Culture Medium

10% FCS, 1% Penicillin-Streptomycin Solution, 2% Glutamine 2% were added to DMEM (final volume –500 ml) and filtered. Medium was kept at 2-8° C. until use.

LPS 10 mg LPS was dissolved in 10 ml sterile water aliquoted and kept at –20° C.

Before use 1 aliquot was defrosted and diluted in culture media to final concentration of 5 ng/ml.

Fish Oil

MW of Fish oil 300 g/mol.

Test items were dissolved in 100% ethanol to form 100 mM concentration.

Further dilutions were made in culture medium. 10% of test item in concentration×10 was added to each well according to study plan.

DIM

MW of DIM is 246 g/mol

Stock solution (100 mM) was prepared in 100% DMSO.

10% of test item in concentration×10 was added to each well according to the study plan.

Before use medium was taken out and pre-warmed at 37° C. bath for minimum 20 min.

BC-Concentrated TQ

Stock solution (100 mM) was prepared in 100% DMSO.

10% of test item in concentration×10 was added to each well according to the study plan.

Before use medium was taken out and pre-warmed at 37° C. bath for minimum 20 min.

Preparation of ELISA Kits Wash (Original×25)

For 1 plate—25 ml wash concentrated (X25) were diluted with 600 ml distilled water to reach 625 m Test Items and LPS (Lipopolysaccharide) Stimulation At day 1, medium was replaced, and the following materials were added in final volume of 1.5 ml, then cells were treated with 5 ng/ml LPS overnight:

After 3 hours of pre-treatment with FO at final concentrations of 15 $\mu$M.

After 3 hours of pre-treatment with DIM at final concentrations of 15 $\mu$M.

After 3 hours of pre-treatment with BC-concentrated TQ at final concentrations of 10 $\mu$M.

After 3 hours of pre-treatment with FO and BC-concentrated TQ at final concentrations of 15 μM and 10 μM, respectively.

After 3 hours of pre-treatment with FO, DIM and BC-concentrated TQ, at final concentrations of 15 μM, 15 μM and 10 μM, respectively.

As a control cells were treated with:

LPS only (with no test material) at time+3

LPS (time 3 h)+DMSO.

Figure 3:
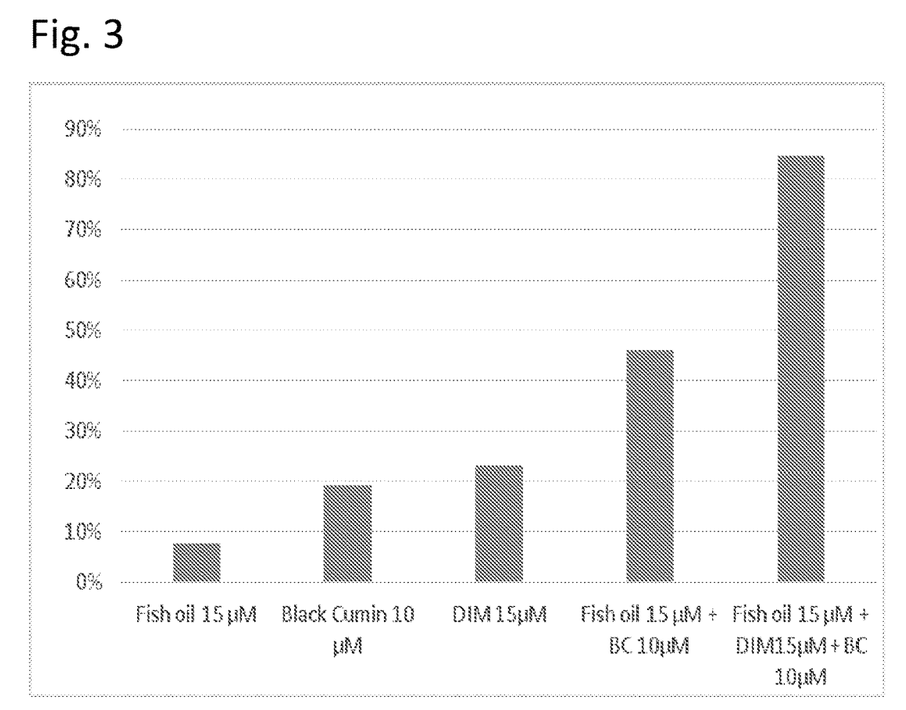
FIG. 3 graphically demonstrates the synergistic interaction seen between TQ and omega-3 fatty acids in a model of NO production in cultured murine macrophages.

The results of this study are shown in the bar graph presented in FIG. 3. It may be seen from this figure that when tested separately, fish oil, high TQ concentration BC and DIM each caused inhibition of NO production by the cultured cells. It is to be further noted that when Fish oil and BC were used in combination, the degree of inhibition of NO production (approximately 45%) was higher than the total of the inhibition caused by each of the two components when tested separately (approximately 28%), Similarly, when fish oil, BC and DIM were used in combination, the degree of NO inhibition caused by that combination (approximately 85%) was greater than the total of the inhibition caused by each of its three components when tested separately (approximately 50%).

These results indicate that there is a synergistic interaction between omega 3 fatty acids, TQ and DIM when used together in various combinations in anti-inflammatory compositions.

Example 5

Screening Study for Synergistic Anti-Inflammatory Effect of Combinations of (i) Omega 3 and BC and (ii) Omega 3, BC and DIM on Carrageenan-Induced Paw Edema Model in Rats The study was carried out by Pharmaseed Ltd.—Israel.

The principle of the study was based on testing the anti-inflammatory effect of the tested items on acute inflammation induced by subcutaneous injection of Carrageenan into rat paw. The effect was evaluated by measurements of the thermal Hyperalgesia in the paw 3 and 6 hours post Carrageenan injection.

Study End Point:

Measurements of response time to thermal stimulus at 3 and 6 hours post Carrageenan administration Clinical Observations A total of 101 rats were utilized. Each tested group included n=10-15 animals. The number of groups and the total number of animals was based on previous studies demonstrating that this is the minimum number of animals per group sufficient to obtain indicative/significant information.

Oral (gavage) was the sponsor's preferred route of administration of the tested items.

MCT (medium chain triglyceride) was used as vehicle to prepare the test item solution Indomethacin was used as reference drug.

Animals

Species/Strain: Rats/Sprague-Dawley (SD)

Gender/Number/Age: Male/101/per weight 175-225 g

Body weight: The minimum and maximum weights of the group did not exceed ±20% of group mean weight of 229 g at study initiation.

Acclimation period: 10-11 days.

Identification: Three position ear notching and cage cards.

Diet: Animals were fed ad libitum a commercial rodent diet (Teklad Certified Global 18% Protein Diet cat #: 106S8216). Animals had free access to acidified drinking water (pH between 2.5 and 3.0) obtained from the municipality supply.

Randomization: Animals were allocated into 4 groups [1. Vehicle (no anti-inflammatory treatment) 2. Positive control (indomethacin). 3BC concentrated TQ+FO, 4. BC concentrated TQ+FO+DIM, according to their body weight.

Duration of the Experimental Period: 18 Days

Time Line

Ten-Eleven days of acclimatization period

Test items loading by daily oral gavages for 10 days

Hot plate test baseline determination

Carrageenan injection

Hot plate test 3 and 6 hours after Carrageenan injection

Procedures:

Following completion of the acclimatization period, the rats were loaded with the tested items orally by gavages for 10 days prior to Carrageenan injection. On day 11, one hour before Carrageenan injection, all animals were tested in the hot plate test to determine the baseline response time of each animal to the thermal stimulus.

Thermal Stimulus Measurements

One hour before the 3 and 6 hours post Carrageenan injection the rats were transported to the testing room and left undisturbed for at least 15 min. before the test. Illumination in the testing room was 100-130 Lux at the level of the bench (red light). The hot plate was maintained thermostatically at a temperature of 50° C. One rat per time was introduced into the hot plate platform and Carrageenan injected and control paw lifting or jump (the response) were retained as criteria. The latency of the response was measured in a blind manner. In absence of response, a 60 sec. cut off is used to prevent tissue damage.

Administration of the Test Material

After the acclimatization, the rats were loaded with the tested items orally by gavages for 10 days prior to Carrageenan injection. Indomethacin was dissolved in saline and given orally by gavages 1 h before carrageenan injection.

Clinical Observations

Clinical observations were performed twice-weekly during the study period. No clinical signs were observed.

Results

Hot Plate test:

Carrageenan-induced inflammation of the rat hind paw is an established model for persistent pain of inflammatory origin. The latency of paw withdrawal to a thermal stimulus was used as an index of inflammatory hyperalgesia in awake rats.

Figure 4:
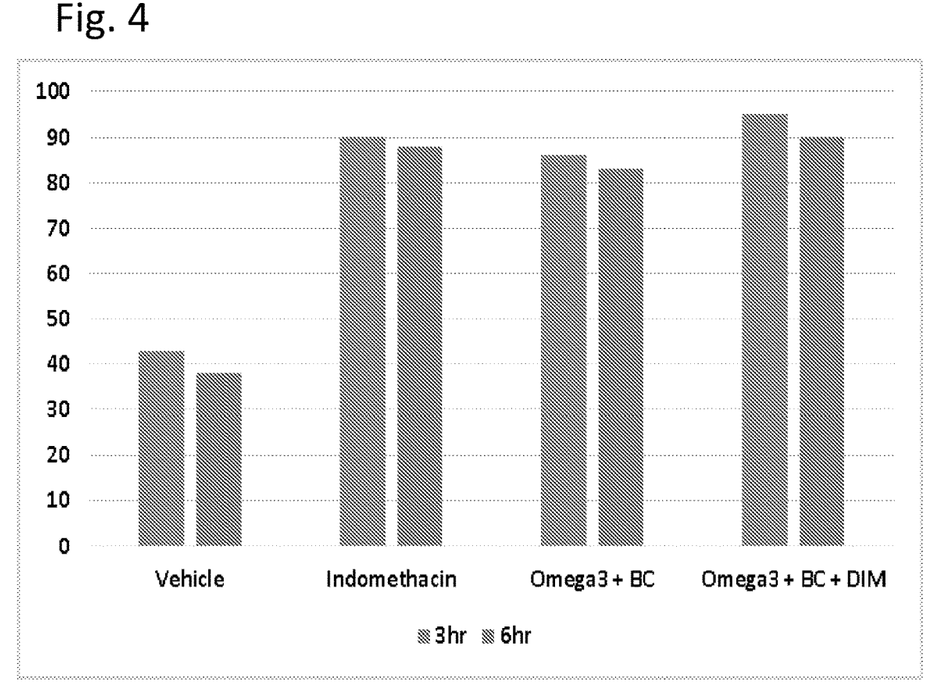
FIG. 4 is at bar graph demonstrating a synergistic anti-inflammatory effect of compositions of the present invention in an in vivo paw edema model in rats.

As shown in FIG. 4, both the composition comprising a combination of Omega 3 and BC concentrated TQ and the combination of Omega 3, BC concentrated TQ and DIM significantly decreased carrageenan-induced thermal hyperalgesia at both 3 hours and 6 hours after carrageenan administration, compared to vehicle treated control. In addition, it may be seen that the magnitude of this effect is similar to that seen with the indomethacin positive control.

Example 6

Effect of Compositions Comprising Different Weight Ratio Combinations of Omega-3 Fatty Acids and TQ on the Production of NO in LPS-Stimulated Cultured Cells In this study, the same model of cultured murine macrophage cells as described in Example 4, hereinabove, was used to determine the effect of varying the ratio of TQ and omega-3 fatty acids on the amount of NO production inhibition observed. The details of the cultured cells and the NO production assay are the same as those provided in Example 4.

The omega-3 fatty acids used in this study were obtained from Kinomega (Product no. 4638 EE (Deyang City, China) containing 46% EPA and 38% DHA in their ethyl ester forms).

TQ was added to the composition in the form of cold-pressed BC oil, supplied by TriNutra, Ness Ziona, Israel, having a TQ concentration of 2% w/w.

The BC oil was tested at a range of dilutions (from 1:200,000 to 1:1,000,000), in combination with three different concentrations of omega-3 fatty acid: 4.4, 8.8 and 17.6 μM.

The molar concentration of TQ in each of these dilutions is given in the following table:

| BC oil dilution | [TQ] μM |
|---|---|
| 1:200,000 | 0.61 |
| 1:300,000 | 0.41 |
| 1:400,000 | 0.31 |
| 1:500,000 | 0.24 |
| 1:700,000 | 0.17 |
| 1:1,000,000 | 0.12 |

The molar ratio of TQ:omega for each of the tested combinations is, therefore, as follows:

| [TQ] μM | [omega] μM | TQ:omega |
|---|---|---|
| 0.61 | 4.4 | 1:7.21 |
| 0.41 | 4.4 | 1:10.73 |
| 0.31 | 4.4 | 1:14.19 |
| 0.24 | 4.4 | 1:18.33 |
| 0.17 | 4.4 | 1:25.88 |
| 0.12 | 4.4 | 1:36.67 |
| 0.61 | 8.8 | 1:14.43 |
| 0.41 | 8.8 | 1:21.46 |
| 0.31 | 8.8 | 1:28.39 |
| 0.24 | 8.8 | 1:36.67 |
| 0.17 | 8.8 | 1:51.76 |
| 0.12 | 8.8 | 1:73.33 |
| 0.61 | 17.6 | 1:28.85 |
| 0.41 | 17.6 | 1:42.93 |
| 0.31 | 17.6 | 1:56.77 |
| 0.24 | 17.6 | 1:73.33 |
| 0.17 | 17.6 | 1:103.53 |
| 0.12 | 17.6 | 1:146.67 |

Figure 5:
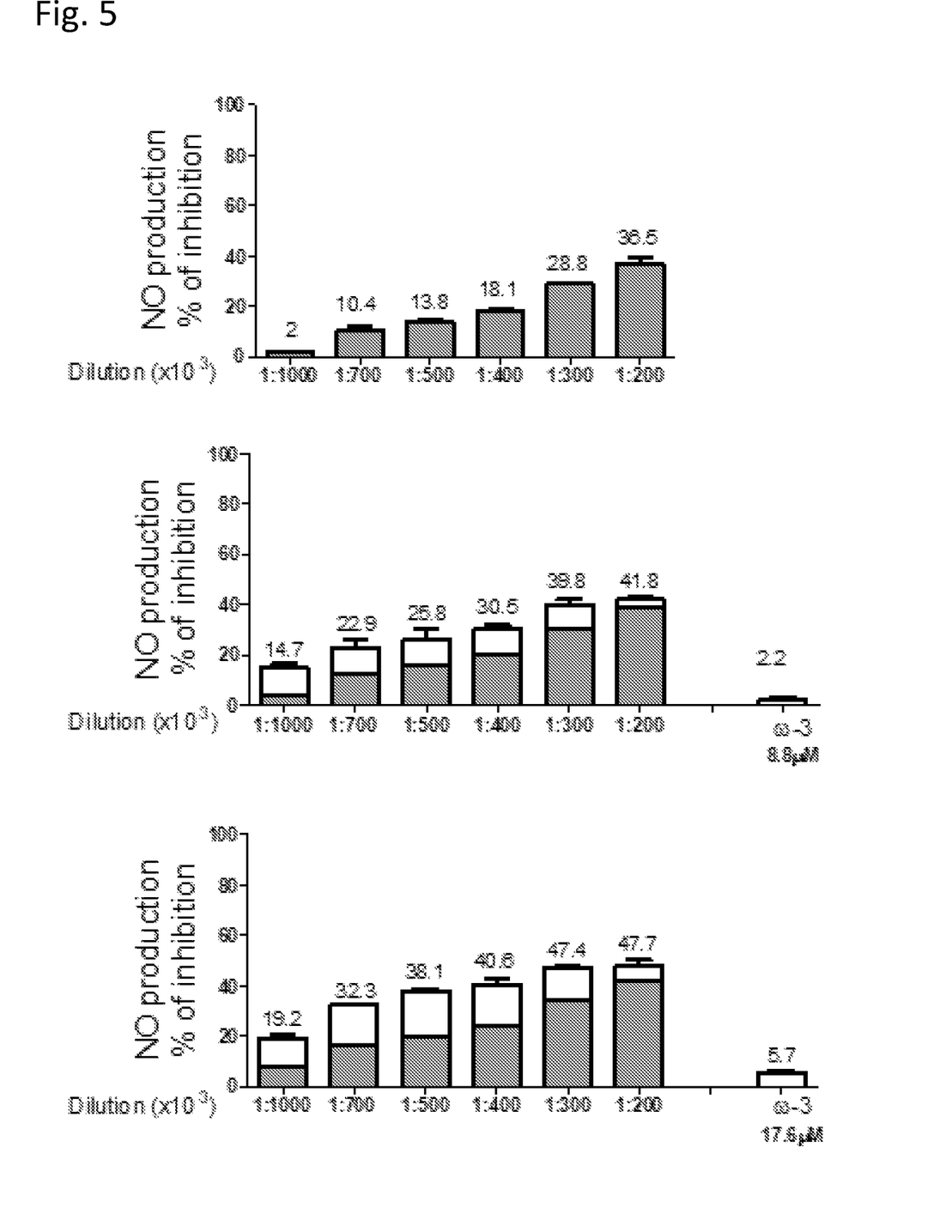
FIG. 5 presents the results of a study comparing compositions of the present invention having different weight ratio combinations of TQ and omega-3 fatty acids (the latter used at concentrations of 8.8 and 17.6 µM) with respect to their synergistic anti-inflammatory activities in an in vitro model of NO release.

FIG. 5 presents three bar graphs summarizing the results for the various BC dilutions tested in combination with omega-3 fatty acids, wherein said fatty acids were present at a concentration of either 8.8 or 17.6 μM. The BC oil dilution factor is shown along the X-axis, while the percentage inhibition of NO production by the treated LPS-stimulated cultured macrophage line is shown on the Y-axis. The percentage inhibition values actually obtained are indicated immediately above each bar.

The upper of the three graphs in FIG. 5 presents the results for the various BC dilutions alone, that is, in the absence of omega-3 fatty acids. The middle of the three graphs presents the results obtained when the TQ (in the BC dilutions) was tested in combination with 8.8 μM omega-3 fatty acid, while the lower graph relates to the combinations containing 17.6 μM omega-3 fatty acid. In the middle and lower graphs of this figure, the height of the greyed-in lower portion of each bar indicates the percentage NO production inhibition that would have been expected from the results obtained for the corresponding concentration of omega-3 fatty acids and TQ, when tested alone (i.e. the expected additive results). Thus, the unshaded upper portion of each bar represents a degree of inhibition that is greater than additive, i.e. a synergistic effect.

It will be noted that at all TQ concentrations tested in combination with either 8.8 or 17.6 μM omega-3 fatty acids, a synergistic anti-inflammatory effect was observed.

Figure 6:
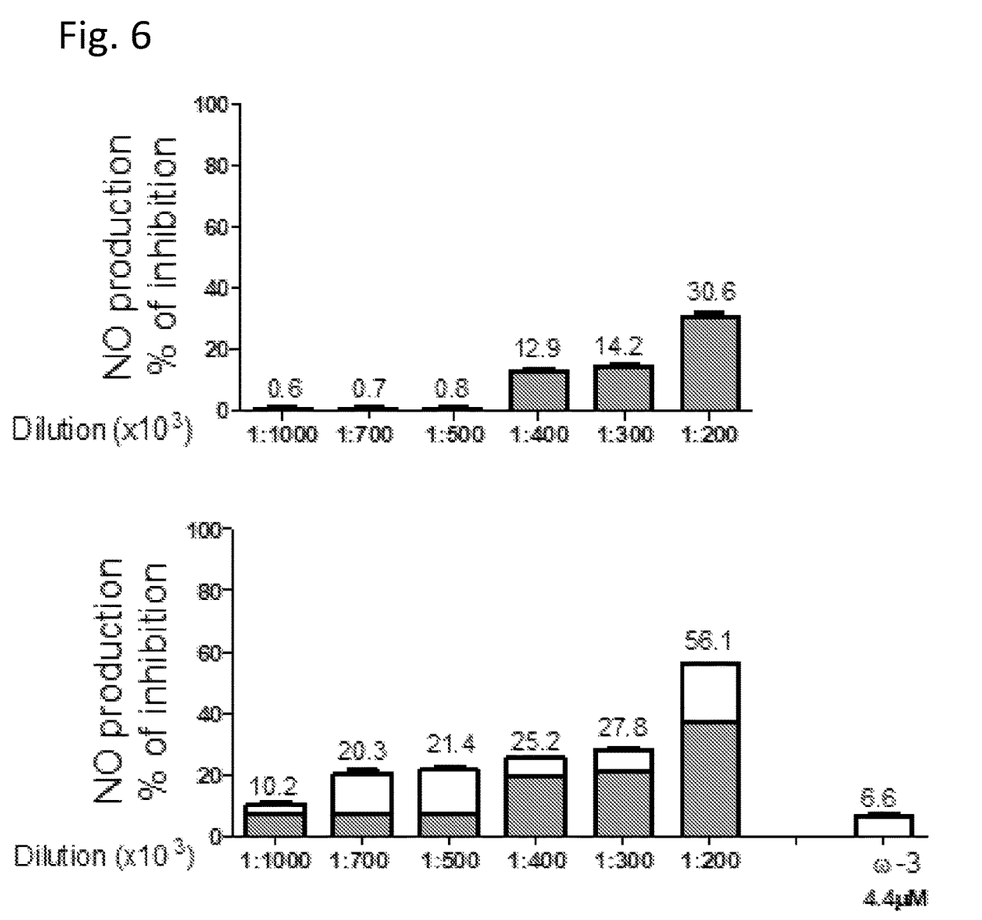
FIG. 6 presents the results of a study comparing compositions of the present invention having different weight ratio combinations of TQ and omega-3 fatty acids (the latter used at a concentration of 4.4 µM) with respect to their synergistic anti-inflammatory activities in an in vitro moxdel of NO release.

A lower concentration of omega-3 fatty acids (4.4 μM) was tested in a separate experiment, using the same conditions as for the study summarized in FIG. 5. The results for the various combinations of TQ (at different concentrations) and this lower omega-3 fatty acid concentration are shown in FIG. 6. As with FIG. 5, the upper graph in FIG. 6 presents the results for the various BC dilutions alone, that is, in the absence of omega-3 fatty acids. Similarly, the lower graph presents the results for the various BC dilutions in combination with the 4.4 μM concentration omega-3. It may be seen from this lower graph that a synergistic effect is observed with all of the combinations tested.

It may be concluded from these results that over the range of TQ:omega-3 fatty acid molar ratios tested, there is an unexpected synergistic interaction between TQ and omega-3 fatty acids, with respect to their ability to inhibit NO production.

Example 7

Effect of Compositions Comprising Combinations of Different Omega-3 Fatty Acid Preparations with TO on the Production of NO in LPS-Stimulated Cultured Cells In this study, the experiments reported in Example 6 were repeated at selected TQ:omega-3 fatty acid ratios using omega-3 fatty acid preparations (obtained from Kinomega, China).

The results for each of a low EPA—high DHA and a high EPA—low DHA omega-3 fatty acid preparation are summarized in the following two tables:

| 10% EPA/74% DHA: | | | |
|---|---|---|---|
| Omega 3 concentration μM | TQ + Omega 3 predicted NO Production % of Inhibition | TQ + Omega 3 Actual NO Production % of Inhibition | TQ:Omega 3 molar ratio |
| 6 | 33.80 | 62 | 1:10 |
| 12 | 37.80 | 79 | 1:20 |
| 24 | 48.80 | 86 | 1:40 |

| 60% EPA/6% DHA: | | | |
|---|---|---|---|
| Omega 3 concentration μM | TQ + Omega 3 predicted NO Production % of Inhibition | TQ + Omega 3 Actual NO Production % of Inhibition | TQ:Omega 3 molar ratio |
| 6 | 37.80% | 55% | 1:10 |
| 12 | 42.80% | 66% | 1:20 |
| 24 | 49.80% | 82% | 1:40 |

In each case, the TQ concentration in the combination was 0.61 μM.

It may be seen from the results presented in these tables that both the low EPA-high DHA and be high EPA-low DHA omega-3 preparations tested, displayed the same unexpected synergistic behavior with regard to NO production inhibition as did the more evenly balanced (46% EPA, 38% DHA) preparation tested in Example 6.

The invention claimed is:

1. A composition comprising a combination of thymoquinone (TQ), and one or more omega-3 fatty acids, wherein the molar ratio between said TQ and said one or more omega-3 fatty acids is equal to or less than 1:7, wherein the TQ and one or more omega-3 fatty acids are present in an effective amount to provide a synergistic anti-inflammatory effect, and wherein the one or more omega-3 fatty acids are highly concentrated oils containing a minimum of 85% w/w DHA & EPA in their ethyl ester forms, and wherein the molar ratio between DHA and EPA is in the range of 1:1000 to 1000:1.

2. The composition according to claim 1, wherein the molar ratio between TQ and the omega-3 fatty acids is in the range of 1:7-1:200.

3. The composition according to claim 1, wherein the molar ratio between TQ and the omega-3 fatty acids is in the range of 1:7-1:150.

4. The composition according to claim 1, wherein the molar ratio between TQ and the omega-3 fatty acids is in the range of 1:7-1:140.

5. The composition according to claim 1, wherein the TQ is present in the composition in a form selected from the group consisting of intact black cumin (BC) seeds, ground BC seeds, BC seed oil, solvent extracts of BC seeds, supercritical $CO_2$ extracts of BC oils, and/or partially purified extracts, purified extracts and/or fractions thereof.

6. The composition according to claim 1, wherein the TQ is synthetic TQ.

7. The composition of claim 1, further comprising 3,3-diindolylmethane (DIM).

8. A dosage form comprising the composition according to claim 1, wherein said dosage form is selected from the group consisting of a soft gelatin capsule, a sprinkle capsule, a sachet, a tablet, a syrup or other pharmaceutically acceptable oral dosage form.

9. The dosage form according to claim 8, wherein the amount of TQ in said dosage form is 1-15% of the amount of omega-3 fatty acid.

10. The dosage form according to claim 8, further comprising 3,3-diindolylmethane (DIM), wherein the amount of TQ in said dosage form is 1-15% of the amount of omega-3 fatty acid and the amount of DIM is 1-15% of the amount of omega-3 fatty acid.

11. A composition according to claim 1, comprising an effective amount of the combination of TQ and one or more omega-3 fatty acids, for the treatment, prevention, attenuation or inhibition of the progression of an inflammatory disease or a disease having an inflammatory component.

12. The composition according to claim 1, in the form of a fixed dose composition, which optionally further comprises a nutritionally or pharmaceutically acceptable ingredient.

13. A unit dosage form, which is a soft gelatin capsule, wherein the soft gelatin capsule comprises: a) 10-200 mg of thymoquinone (TQ); and b) 300-900 mg of highly concentrated DHA & EPA ethyl esters, with a molar ratio of EPA/DHA ranging from 1:2 to 2:1.

14. The unite dosage form of claim 13, wherein the soft gelatin capsule further comprises one or more ingredients selected from:
 c) 1-20 mg lycopene or lutein;
 d) 4-8 mg of vitamin E; and
 e) a surface active material.

* * * * *